(12) United States Patent
Lomeli et al.

(10) Patent No.: US 12,396,764 B2
(45) Date of Patent: *Aug. 26, 2025

(54) CONTROL MEMBER FOR ADJUSTING ACCESS TUBE POSITION, AND RELATED SYSTEMS AND METHODS

(71) Applicant: Medos International Sarl, Le Locle (CH)

(72) Inventors: Roman Lomeli, Plymouth, MA (US); John C. Voellmicke, Franklin, MA (US); Paul S. Maguire, Hope Valley, RI (US); Clara Cheung, Quincy, MA (US)

(73) Assignee: Medos International Sarl, Le Locle (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/435,017

(22) Filed: Feb. 7, 2024

(65) Prior Publication Data
US 2024/0173055 A1    May 30, 2024

Related U.S. Application Data

(63) Continuation of application No. 16/692,342, filed on Nov. 22, 2019, now Pat. No. 11,944,356.

(51) Int. Cl.
*A61B 17/70* (2006.01)
*A61B 17/02* (2006.01)
*A61B 17/34* (2006.01)

(52) U.S. Cl.
CPC ...... *A61B 17/7076* (2013.01); *A61B 17/0218* (2013.01); *A61B 17/3423* (2013.01); *A61B 2017/3445* (2013.01); *A61B 2560/0425* (2013.01)

(58) Field of Classification Search
CPC ............ A61B 17/7076; A61B 17/0218; A61B 17/3423; A61B 2017/3445; A61B 2560/0425
See application file for complete search history.

(56) References Cited

U.S. PATENT DOCUMENTS

| | | | |
|---|---|---|---|
| 7,198,598 B2 | 4/2007 | Smith et al. | |
| 7,578,820 B2 | 8/2009 | Moore et al. | |
| 7,699,864 B2 | 4/2010 | Kick et al. | |

(Continued)

OTHER PUBLICATIONS

U.S. Appl. No. 16/692,342, filed Nov. 22, 2019, entitled ontrol Member for Adjusting Access Tube Position, and Related Systems and Methods.

(Continued)

*Primary Examiner* — Tracy L Kamikawa
(74) *Attorney, Agent, or Firm* — BakerHostetler

(57) ABSTRACT

A control member for mounting to an end of an access tube includes a body that defines a proximal end and a distal end spaced from each other along a central axis. The control member defines a bore extending between the proximal and distal ends along the central axis, a handle portion that extends to the proximal end, and a mounting formation that extends to the distal end. The mounting formation includes an insertion portion that is insertable within the access tube and a lip that is opposed to the insertion portion so as to define a receptacle configured to receive an end portion of the access tube.

20 Claims, 8 Drawing Sheets

(56) References Cited

U.S. PATENT DOCUMENTS

| | | |
|---|---|---|
| 8,372,131 B2 | 2/2013 | Hestad et al. |
| 8,622,897 B2 | 1/2014 | Raymond et al. |
| 8,721,536 B2 | 5/2014 | Marino et al. |
| 8,998,807 B2 | 4/2015 | Fiorella |
| 9,265,491 B2 | 2/2016 | Lins et al. |
| 9,387,313 B2 | 7/2016 | Culbert et al. |
| 9,393,057 B2 | 7/2016 | MacMillan et al. |
| 9,615,818 B2 | 4/2017 | Baudouin et al. |
| 9,795,367 B1 | 10/2017 | Lee et al. |
| 9,867,605 B2 | 1/2018 | Adams |
| 9,895,164 B2 | 2/2018 | Kleyman |
| 9,980,744 B2 | 5/2018 | Corbin et al. |
| 9,980,771 B2 | 5/2018 | Carter et al. |
| 10,413,324 B2 | 9/2019 | Kleyman et al. |
| 10,869,660 B2 | 12/2020 | Berry |
| 11,944,356 B2 * | 4/2024 | Lomeli ............... A61B 17/7076 |
| 2004/0002629 A1 | 1/2004 | Branch et al. |
| 2005/0137461 A1 | 6/2005 | Marchek et al. |
| 2005/0137609 A1 | 6/2005 | Guiraudon |
| 2006/0200186 A1 | 9/2006 | Marchek et al. |
| 2007/0016223 A1 | 1/2007 | Pagliuca et al. |
| 2007/0038033 A1 | 2/2007 | Jones et al. |
| 2008/0132766 A1 | 6/2008 | Dant et al. |
| 2008/0161650 A1 | 7/2008 | Hestad et al. |
| 2008/0214898 A1 | 9/2008 | Warren |
| 2013/0116510 A1 | 5/2013 | Lutze et al. |
| 2014/0121467 A1 | 5/2014 | Vayser et al. |
| 2015/0359570 A1 | 12/2015 | Ries |
| 2016/0270816 A1 | 9/2016 | Mather et al. |
| 2017/0238962 A1 | 8/2017 | Hansen et al. |
| 2018/0008253 A1 | 1/2018 | Thommen et al. |
| 2018/0125603 A1 * | 5/2018 | Cantor .................. A61B 90/57 |
| 2018/0153592 A1 | 6/2018 | Larson |
| 2019/0183476 A1 | 6/2019 | Garcia-Bengochea et al. |
| 2019/0209154 A1 | 7/2019 | Richter et al. |
| 2021/0153914 A1 | 5/2021 | Lomeli et al. |
| 2021/0186477 A1 | 6/2021 | Buehlmann et al. |

OTHER PUBLICATIONS

U.S. Appl. No. 16/722,480, filed Dec. 20, 2019, entitled "Retractor Member, and Related Systems and Methods.".

* cited by examiner

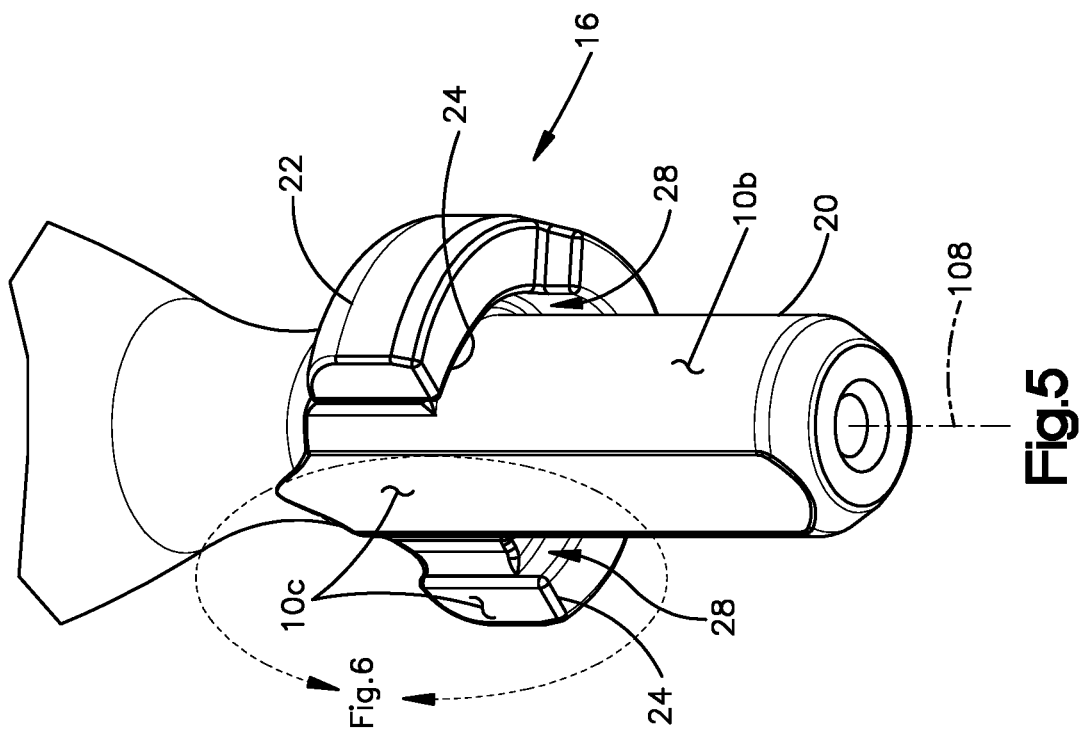
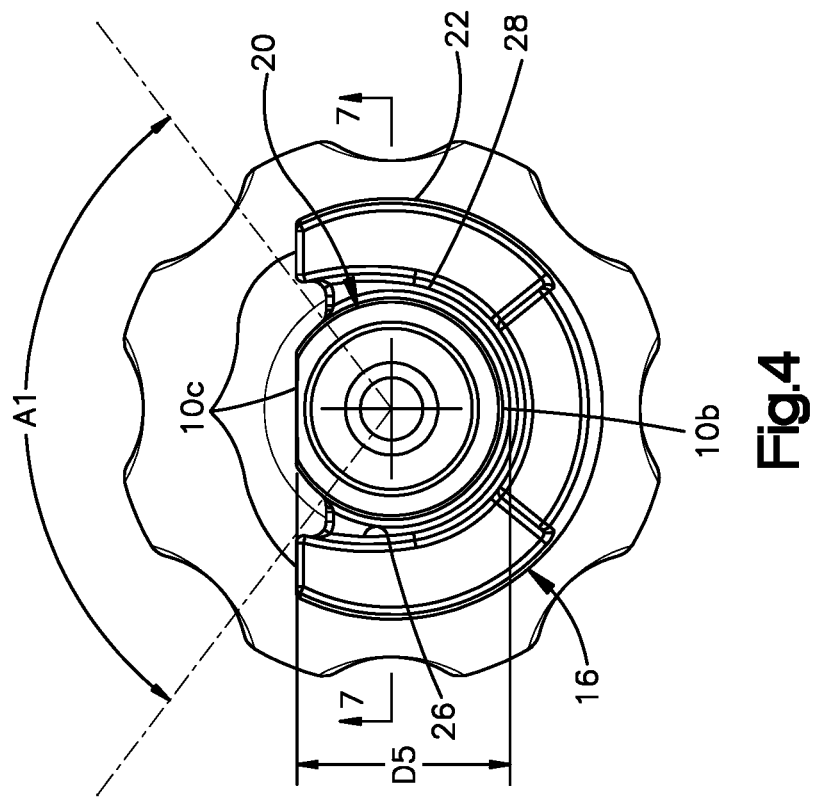

CONTROL MEMBER FOR ADJUSTING ACCESS TUBE POSITION, AND RELATED SYSTEMS AND METHODS

CROSS REFERENCE TO RELATED APPLICATIONS

This application is a continuation of U.S. application Ser. No. 16/692,342 filed Nov. 22, 2019, now U.S. Pat. No. 11,944,356, the contents of which is hereby incorporated by reference in its entirety.

TECHNICAL FIELD

The present invention relates to devices for manipulating an access tube, as well as to systems and methods related to manipulating an access port.

BACKGROUND

Access tubes and/or retractors can be used to provide a surgeon with an access portal or "working channel" to a surgical treatment site within patient anatomy. Various minimally invasive procedures, including spinal procedures such as decompression, fusion, external fixation, and the like may be performed through such access portals. The access tubes used in these procedures must often be secured in position relative to the treatment site via external devices, such as operating table-mounted devices and/or anatomical-mounted devices, such as bone anchors, including pedicle anchors and the like, by way of non-limiting examples. Once the access tube is positioned relative to the patient anatomy, repositioning the access tube during surgery can be awkward, cumbersome, and time-consuming, and can often require removal of one or more and up to each of the surgical instruments extending through the access tube toward the treatment site.

SUMMARY

According to an embodiment of the present disclosure, a control member for mounting to an end of an access tube includes a body that defines a proximal end and a distal end spaced from each other along a central axis. The body also defines a bore extending between the proximal and distal ends along the central axis, a handle portion that extends to the proximal end, and a mounting formation that extends to the distal end. The mounting formation includes an insertion portion that is insertable within the access tube and a lip that is opposed to the insertion portion so as to define a receptacle therebetween. The receptacle is configured to receive an end portion of the access tube.

According to another embodiment of the present disclosure, a surgical access system includes a tubular body having a distal end and a proximal end spaced from the distal end in a proximal direction. The tubular body defines a channel extending from the proximal end to the distal end in a distal direction opposite the proximal direction. The system includes a control member having a first end and a second end opposite one another. The control member defines a handle portion at the first end and a mounting formation at the second end. The mounting formation is configured to mount to the proximal end of the tubular body and includes an insertion portion that is configured to reside within the channel when the control member is mounted to the tubular body. The mounting formation also includes a lip opposed to the insertion portion so as to define a receptacle therebetween. The receptacle is configured to receive the proximal end of the tubular body such that the mounting formation interlocks with the tubular body and the handle portion extends from the proximal end of the tubular body in the proximal direction.

According to an additional embodiment of the present disclosure, a method of adjusting a position of an access tube that extends distally from an ex vivo location, through the skin line, and to a target location with patient anatomy includes attaching a control member to a proximal end of the access tube such that a central axis of the control member extends through a working channel of the access tube while remaining spaced from each inner surface of the access tube, and also includes manipulating the control member, thereby responsively adjusting a trajectory of the working channel relative to the patient anatomy.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 4 is a bottom plan view the control member illustrated in FIG. 2, showing a plan view of the mounting formation;

FIG. 5 is an enlarged perspective view of a mounting formation of the control member illustrated in FIG. 2;

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The embodiments described below pertain to control devices for adjusting the position of a working channel within patient anatomy. In particular, the control devices described herein are configured to angulate the working channel polyaxially, whereby the orientation of a central axis of the working channel can be adjusted relative to the patient anatomy so as to intersect a target location within the anatomy. The control devices described herein can also adjust the rotational position of the access tube (and thus also of the working channel) about the central axis. The control devices are also configured for ease of attachment to and detachment from the access tube, such that, while attached, the control device can provide the foregoing positional adjustments. Moreover, the control devices described herein each define at least one access opening that is aligned with and open to the working channel while the control device is coupled to the access tube.

Figure 1A:
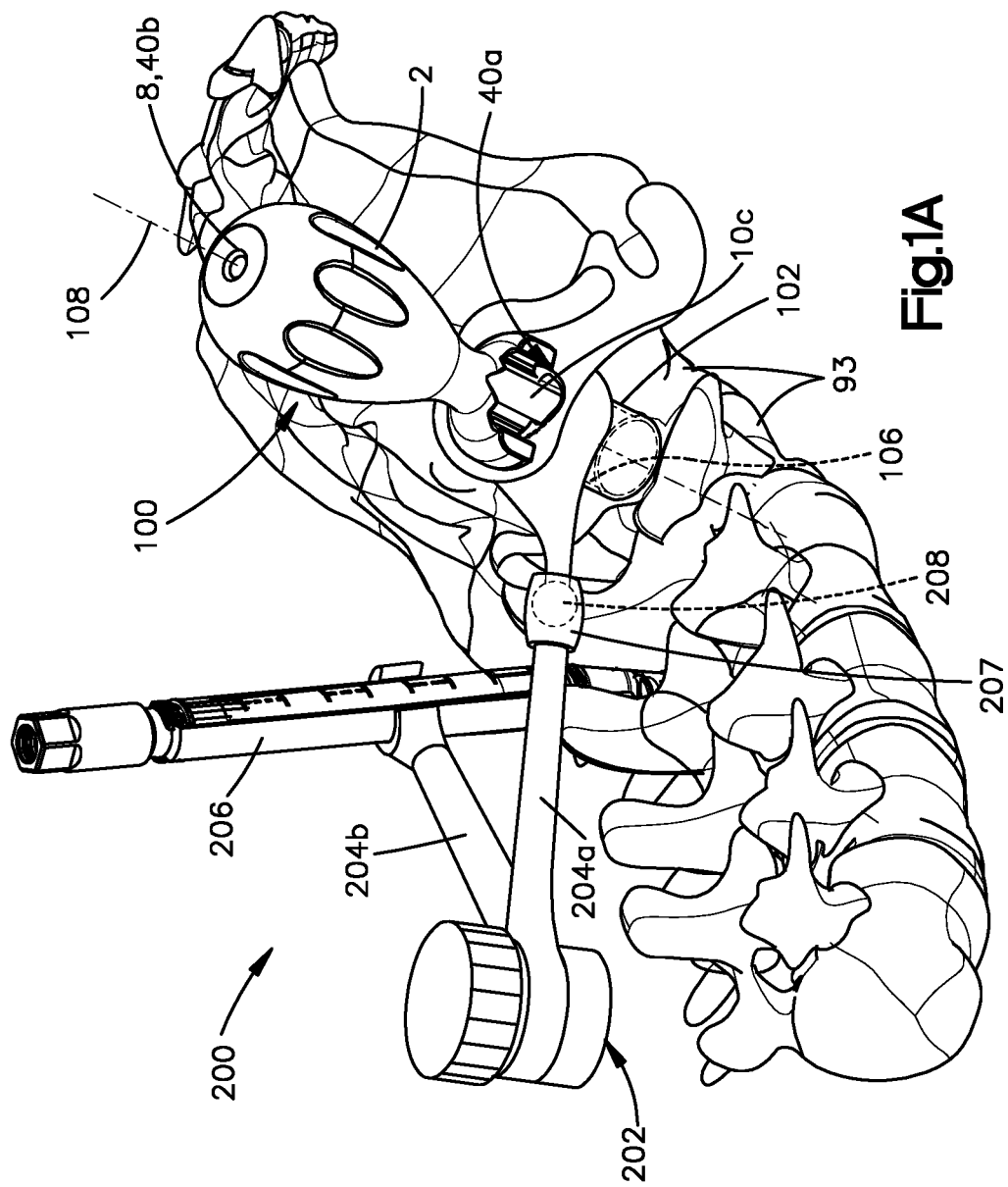
FIG. 1A is a perspective view of a spinal surgical system that includes a surgical access system, according to an embodiment of the present disclosure.
Figure 1B:
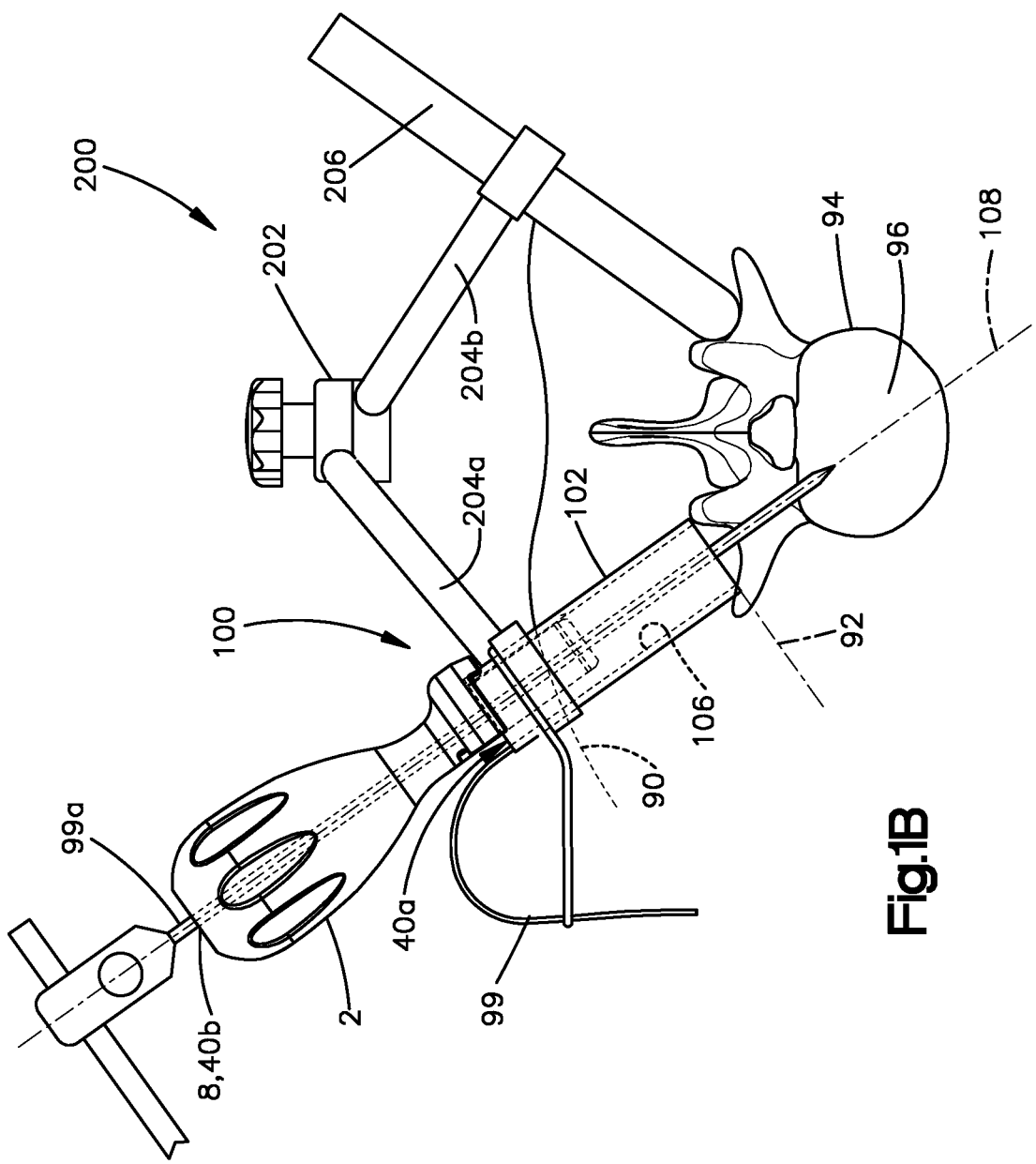
FIG. 1B is another perspective view of the spinal surgical system illustrated in FIG. 1A, additionally showing a navigated instrument employed with the surgical access system, according to an embodiment of the present disclosure.

Referring now to FIGS. 1A and 1B, an exemplary embodiment of a surgical access system 100 includes a tubular body 102, also referred to herein as an "access tube" 102, and a control member 2 configured to adjust the position of the access tube 102. The access tube 102 is configured to extend distally from an ex vivo location with respect to patient anatomy to an in vivo target location within the patient anatomy. By way of a non-limiting example, the access tube 102 can be configured to extend from the ex vivo location and through the skin line 90 and to the target location, which is at or adjacent to an intended surgical treatment site. As shown in FIG. 1B, in the illustrated example, the target location of the access tube 102 is at the facet line 92 of adjacent vertebral bodies 94, and the treatment site includes the intervertebral disc space 96. With the access tube 102 positioned at the proper depth and orientation so as to extend to the treatment site, a central axis 108 of the surgical access system 100 intersects the treatment site. In this manner, instrumentation 99 can be advanced distally through the access tube 102 and reach the treatment site.

The access tube 102 defines an internal port or channel 106, also referred to herein as a "working channel" 106, that is elongate along the central axis 108 and is open from the ex vivo location to the target location. Accordingly, the working channel 106 provides the instrumentation 99 with access at least to the target location and possibly also to the treatment site. Accordingly, with the surgical instrumentation 99 extending through the working channel 106, a physician can manipulate the portions of the instrumentation 99 proximal of the access tube 102 so as to prepare or otherwise treat the treatment site. The control member 2 is configured to couple with the access tube 102 and adjust the position of the access tube 102 as needed, such as to maintain the intersection of the central axis 108 with the treatment site.

Additionally, the control member 2 has a geometry that is configured to provide ingress and egress of instrumentation 99 to and from the working channel 106 as needed while the control member 2 is coupled to (i.e., is in a "coupled configuration" with) the access tube 102. For example, the control member 2 has a geometry that defines at least one and preferably a plurality of ports or openings into the working channel 106 while the control member 2 is coupled to the access tube 102. In particular, as shown in FIG. 1A, the control member 2 of the illustrated embodiment has an access surface 10c that at least partially defines a first opening 40a into the working channel 106. Additionally, the depicted control member 2 defines a central bore 8 that provides a second opening 40b into the working channel 106. As shown in FIG. 1B, surgical instrumentation 99 can be advanced through the first opening 40a and/or the second opening 40b as needed. In the illustrated example, one or more cables, such as camera and/or irrigation cables, can extend through the first opening 40a, while the second opening 40b (i.e., the central bore 8) can be employed to receive and guide a navigated instrument to the target site, such as the "multi-tool" more fully described in U.S. Patent Publication No. 2018/0008253 A1, published Jan. 11, 2018, entitled "MULTI-SHIELD SPINAL ACCESS SYSTEM" ("the '253 Reference"), the entire disclosure of which is incorporated by reference herein. The multi-tool 99a is elongate along the longitudinal direction X and preferably has an outer diameter that is complimentary with an inner diameter of the central bore 8 such that the central bore 8 substantially aligns a trajectory of the multi-tool 99a along the central axis 108 while the multi-tool 99a extends through the central bore 8.

The surgical access system 100 can be employed as a secondary system or assembly within a primary surgery system 200, such as a spinal fusion surgery system, by way of a non-limiting example. In the illustrated example embodiment, the primary surgery system 200 includes a connector 202 having one or more arms 204, such as first and second arms 204a, b. The first arm 204a can be coupled to the access system 100, particularly to the access tube 102 thereof, and the second arm 204b can be coupled to an anchor, such as a pedicle anchor, such as a contra-lateral pedicle anchor 206. As shown, the first arm 204a can include a joint member, such as a socket 207, which can be coupled to a complimentary joint member, such as a ball 208, of an articulation member 210. The articulation member 210 can, in turn, be coupled to the access tube 102, preferably via a rigid connection, which preferably allows for selective attachment with and detachment from the access tube 102. In the illustrated embodiment, the ball 208 and socket 207 cooperatively allow the access tube 102 to articulate polyaxially relative to the arm 204*a*. The socket 207 can be configured to selectively iterate between a locked position and an unlocked position with respect to the ball 208, each while retaining or "holding" the ball within the socket 207. In the unlocked position, the ball 208 (and thus the articulating member 210 and thus also the coupled access tube 102) can articulate polyaxially relative to the socket 207. In the locked position, the ball 208 (and thus also the access tube 102) is substantially prevented from articulating relative to the socket 207. In this manner, the position of the access tube 102 and its working channel 106 can be affixed relative to the patient anatomy, such as via the anchor 206 and the connector 202. The spinal surgery system 200 can be configured as more fully described in the '253 Reference.

The control member 2 is configured for adjusting, controlling, or otherwise manipulating the trajectory of the access tube 102 within the patient anatomy, and also the rotational orientation of the access tube 102 about the central axis 108, for example, in clockwise and counterclockwise directions relative to the physician. It should be appreciated that the control member 2 can be configured to polyaxially angulate the access tube 102 concurrently with (i.e., substantially simultaneously with) rotating the access tube 102 about the central axis 108. In this manner, the control member 2 allows the physician to adjust the position of the access tube 102, and thus also the position of the working channel 106, relative to the patient anatomy as needed during a surgical procedure.

Figure 2:
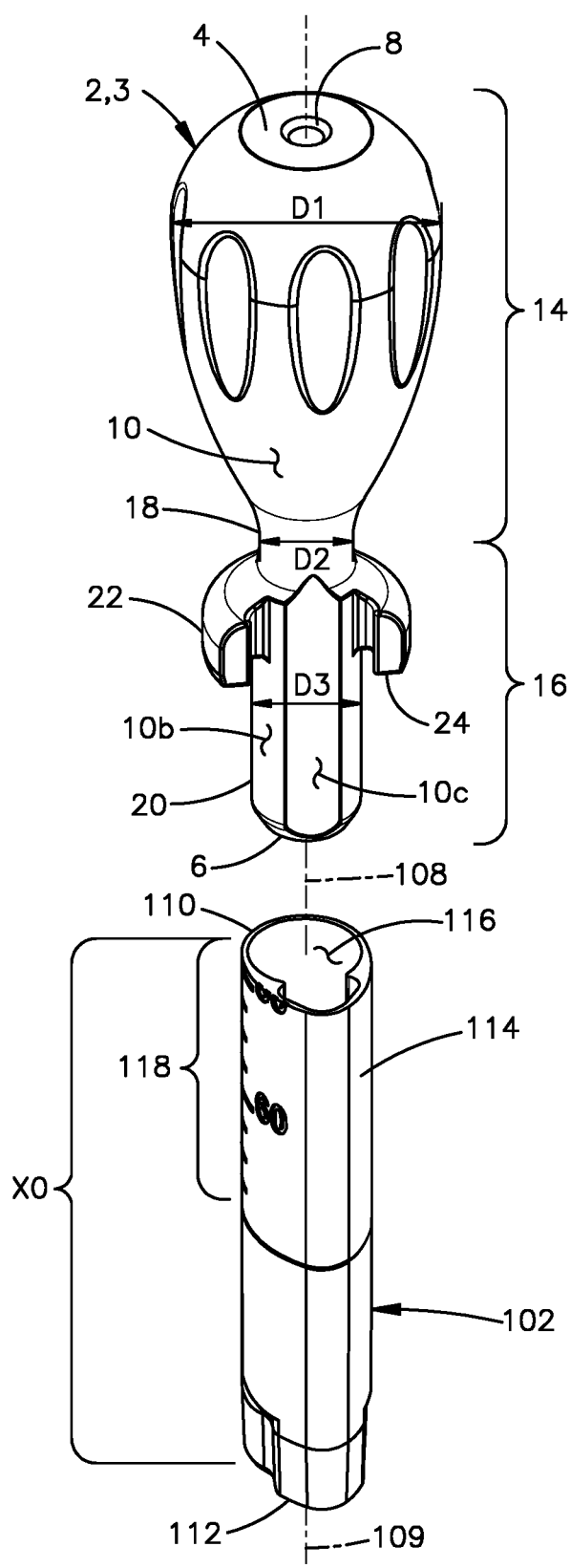
FIG. 2 is a perspective, exploded view of the surgical access system illustrated in FIG. 1A, illustrating an access tube and a control member of the surgical access system, according to an embodiment of the present disclosure.
Figure 3:
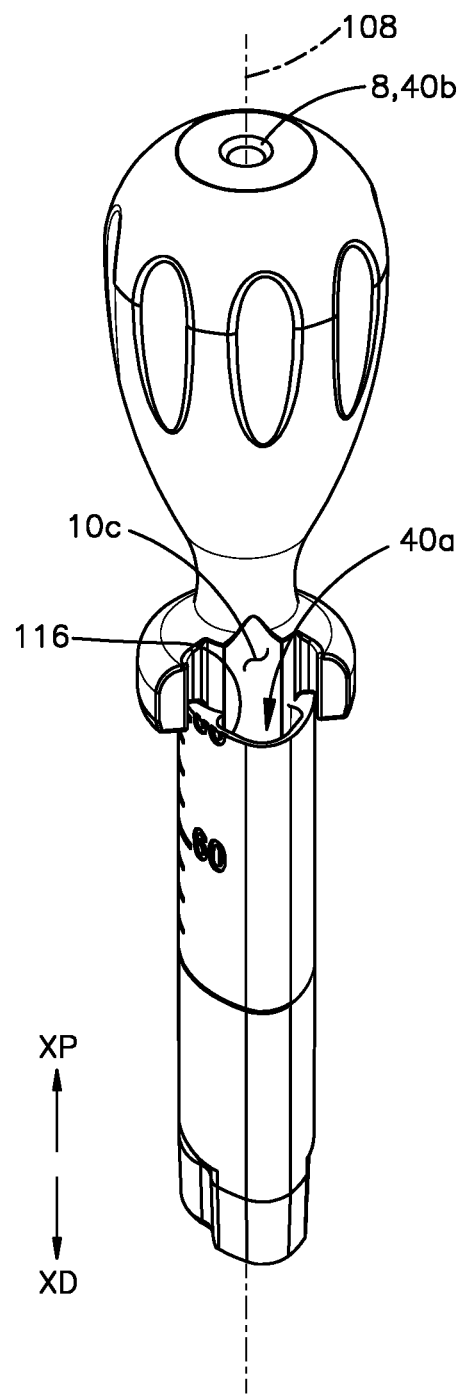
FIG. 3 is a perspective view of the control member and the access tube illustrated in FIG. 2 coupled together.

Referring now to FIGS. 2 and 3, the access tube 102 includes a proximal end 110 and a distal end 112 spaced from each other along a longitudinal direction X, along which the central axis 108 is oriented. In particular, the distal end 112 is spaced from the proximal end 110 along a distal direction XD, while the proximal end 110 is spaced from the distal end 112 along a proximal direction XP. It is to be appreciated that the distal and proximal directions XD, XP are each mono-directional components of the longitudinal direction X, which is bi-directional. The access tube defines a total length X0 measured between the proximal and distal ends 110, 112 along the longitudinal direction X. The access tube 102 defines an outer surface 114 and an inner surface 116 spaced from each other along a radial direction R perpendicular to the central axis 108. In particular, at least a portion of the access tube 102 at the proximal end 110 thereof defines a radial thickness R1 (see FIG. 7) measured between the outer and inner surfaces 114, 116 along the radial direction R. The inner surface 116 defines the working channel 106. The outer and inner surfaces 114, 116 each extend from the proximal end 110 to the distal end 112 of the access tube 102. The outer surface 114 can include visual indicia, such as graduated hash marks or the like, for providing a visual reference for the depth at which the distal end 112 is inserted within the patient, for example.

The access tube 102 is elongate along a channel axis 109 that extends through the working channel 106 and defines the trajectory of the access tube 102 (and thus also the trajectory of the working channel 106). In the illustrated embodiment, when in the coupled configuration, the central axis 108 and the channel axis 109 are substantially parallel, and can optionally be coincident. Accordingly, when in the coupled configuration, manipulating the control member 2 to reposition the trajectory of the central axis 108 also repositions the trajectory of the channel axis 109. Additionally, the central axis 108 preferably remains spaced from the inner surface 116 of the access tube 102 (i.e., the central axis 108 preferably does not intersect the inner surface 116). In this manner, the central axis 108 and the channel axis 109 are aligned and each intersect the target location.

The control member 2 includes a proximal or first end 4 and a distal or second end 6 spaced from each other along the longitudinal direction X, such that the second end 6 is spaced from the first end 4 along the distal direction XD while the first end 4 is spaced from the second end 6 along the proximal direction XP. The control member 2 includes a body 3 that defines the central bore 8, which extends from the first end 4 to the second end 6. In the illustrated embodiment, the central axis 108 extends centrally through the central bore 8. Thus, it can be said that the central bore 8 defines the central axis 108 of the surgical access system 100. The control member 2 has an outer surface 10 spaced from the central bore 8 along the radial direction R. The control member body 3 is formed of a material that is biocompatible, sterilizable (e.g., steam sterilizable), and also radiolucent, such as a polymeric material, including polyphenylsulfone, polysulfone, polyetheretherketone (PEEK), polyethylene (PE), high-density polyethylene (HDPE), polycarbonate, polyetherimide (PEI), polybutylene (PBT), a polyphenylene oxide/polystyrene alloy (PPO/OS), and polythalamide (PPA), by way of non-limiting examples. The material can alternatively be a metal, such as aluminum, or a composite material, such as one that includes a matrix comprising of any of the foregoing polymeric materials and glass-fill or other fibers disposed in the polymeric matrix. The material of the control member body 3 is also preferably lightweight, such as Radel® brand polyphenylsulfone, ULTEM® brand PEI, and polysulfone, by way of non-limiting examples, so as not to be heavy enough to risk causing the access tube 102 to reposition via gravity.

The control member 2 includes a handle portion 14 at the first end 4 and a mounting formation 16 at the second end 6. The handle portion 14 is configured to provide purchase for a physician's hand. The mounting formation 16 is configured to provide a quick, sturdy coupling with the proximal end 110 of the access tube 102. An entirety of the handle portion 14 can be spaced from an entirety of the mounting formation 16 with respect to the longitudinal direction X, although there can be longitudinal overlap between the handle portion 14 and the mounting formation 16 in other embodiments. As shown, the control member 2 can define a neck 18 between the handle portion 14 and the mounting formation 16. It is to be appreciated that the neck 18 can provide enhanced purchase for manual manipulation, such as by being gripped between the physician's thumb and forefinger. The outer surface 10 within the handle portion 14 can have a circular cross-sectional shape in a plane orthogonal to the central axis 108. The handle portion 14 can define a maximum handle diameter D1 and the neck 18 can define a minimum neck diameter D2 that is less than the maximum handle diameter D1. A ratio of the maximum handle diameter D1 to the minimum neck diameter D2 can be in the range of about 1:1 to about 5.0:1, and more particularly in a range from about 2.5:1 to about 3.0:1. It should be appreciated that the ratio can optionally be greater than 5.0:1, and can optionally be less than 1.1:1.

The outer surface 10 within the handle portion 14 can include grip-enhancement formations, such as knurls or the like, for increasing the manipulability of the control member 2. The control member 2 is preferably configured such that, when coupled to the access tube 102, the handle portion 14 extends from the proximal end 110 of the access tube 102 in the proximal direction XP, such that the central axis 108 extends through the central bore 8 and through the working channel 106, from the proximal end 4 of the control member 2 to the distal end 112 of the access tube 110, without being intersected or obstructed by any portion of the access tube 102 or the control member 2. In this manner, the central bore 8 of the control member 2 can provide the physician with an unobstructed view of the working channel 106 and the treatment site through the control member 2 while it is coupled with the access tube 102. The view provided through the central bore 8 can assist the physician with manipulating the control member 2 to adjust the trajectory of the central axis 108. The central bore 8 also provides a straight, unobstructed access path for surgical instrumentation 99 to extend through the control member 2 and to the treatment site. Thus, the central bore 108 can allow the physician to locate the center of the working channel 106 visually and with navigated instrumentation.

Figure 7:
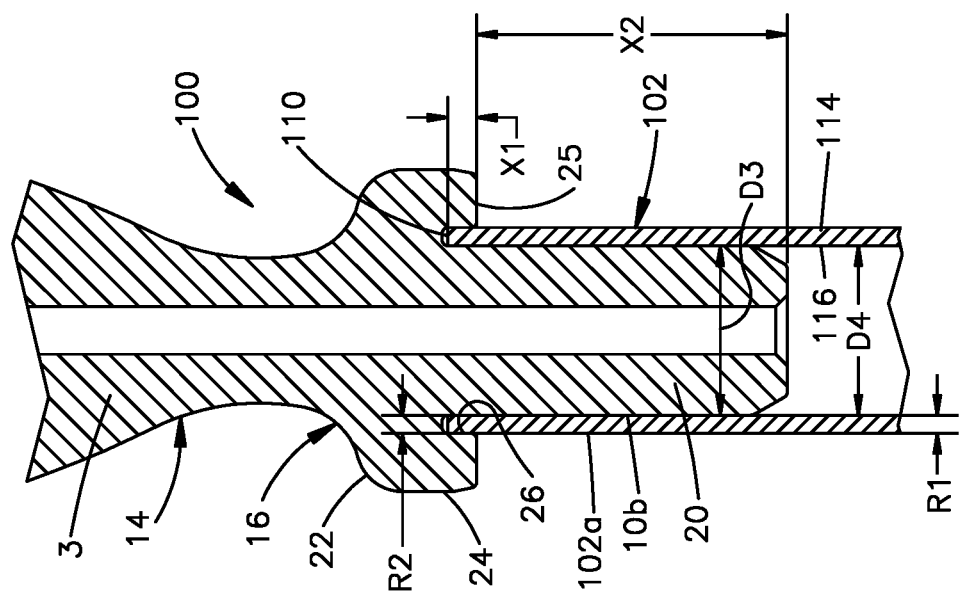
FIG. 7 is a sectional front view of the control member and access tube coupled together as shown in FIG. 3 and taken along section line 7-7 shown in FIG. 4.

The mounting formation 16 has an insertion portion 20 that is configured to reside within the working channel 106 when in the coupled configuration. The insertion portion 20 can have a generally cylindrical shape and can also be referred to as a "mounting post" or a "post" 20. An outer surface 10b of the post 20 can have a cylindrical shape, although other shapes are within the scope of the present disclosure. In the illustrated embodiment, the outer surface 10b of the post is cylindrical and defines a major diameter D3 of the post 20. The outer surface 10b of the post 20 is configured to engage at least a portion of the inner surface 116 of the access tube 102. Accordingly, the inner surface 116 of the access tube 114, or at least a portion thereof, can define an inner diameter D4 that is complimentary with the major diameter D3 of the post 20, as shown in FIG. 7 and discussed in more detail below. The mounting formation 16 also includes a radial protrusion or flange 22 and a lip 24 that extends from the flange 22 in the distal direction XD, as described in more detail below.

With reference to FIGS. 4 and 5, the flange 22 and the lip 24 can be contiguous with the access surface 10c. For example, the flange 22, the lip 24 can define respective portions of the access surface 10c, and thus can also define respective portions of the first opening 40a. As shown, the flange 22 and the lip 24 can extend circumferentially between the access surface 10c less than a full revolution about the central axis 108. Thus, the mounting formation 16 can define a maximum opening angle A1 that comprises the remainder of the full revolution about the central axis 108. Thus, the maximum opening angle A1 can be characterized as the angle about which the lip 24 and the flange 22 do not extend about the central axis 108. In the illustrated embodiment, the maximum opening angle A1 can be measured from the lip 24 and/or the flange 22 at circumferentially opposed portions of the access surface 10c. The maximum opening angle A1 can be sized such that the mounting formation does not interfere with at least a portion of the working channel, such as the opening 40a. For example, the maximum opening angle A1 can be in a range of about 20 degrees to about 180 degrees, and particularly in a range of about 60 degrees to about 135 degrees, and more particularly in a range of about 75 degrees to about 120 degrees. Stated differently, the maximum opening angle A1 can be greater than or equal to 20 degrees but less than or equal to 180 degrees. In this manner, the mounting formation 16 can define the access surface 10c, which in the present embodiment is a face that is configured to be located radially inward of, and opposed to, the inner surface 116 of the access tube 102 so as to define the first access opening 40a into the working channel 106 when the control member 2 is mounted to the access tube 102, as shown in FIG. 3.

As depicted, the face 10c can be substantially planar and can traverse substantially an entirety of a longitudinal length of the post 20. The post 20 can define a minor distance D5, measured from the face 10c to the outer surface 10b of the post 20 along a radial direction R that is also orthogonal to the face 10c. The minor distance D5 of the post 20 is less than the major diameter D3 so as to at least partially define a radial space for the first opening 40a into the working channel 106. A ratio of the minor distance D5 to the major diameter D3 of the post 20 can be in a range of 0.50:1 to about 1:1, and more particularly in a range of about 0.90:1 to about 0.92:1. The face 10c can also be substantially devoid of abrupt edges or other like features that could "catch" or otherwise interfere with insertion and/or removal of instrumentation through the first opening 40a.

With reference to the spinal fusion surgery system 200 described above, the first opening 40a can be configured for ingress and egress of cameras, cables, irrigation, and navigated instruments, by way of non-limiting examples, through the working channel 106 and to the treatment site. Thus, the maximum opening angle A1 and diameters D3-D5 are sized so that the access opening 40a can accommodate such instrumentation (e.g., a camera and camera cable(s)) for use within the working channel 106. It is to be appreciated that a wide variety of surgical instruments can be inserted and removed as needed through the first and second openings 40a, b, according to the needs of the particular surgical procedure in which the surgical access system 100 is employed. The radiolucency of the access tube 102 and the control member 2 allows an enhanced view of such instruments employed with the surgical access system 100 under radioscopy (at least those instruments having radiopaque features). Additionally, with the access tube 102 affixed relative to the patient anatomy, such as via the anchor 206 and the connector 202, the control member 2 can be detached from the access tube 102 and additional or alternative instrumentation can be inserted through the working channel 106, including but not limited to dilators, retractor blades, resection instruments, bone graft delivery instruments, and fusion cage delivery instruments, by way of non-limiting examples. It should be appreciated that the first and second openings 40a, b into the working channel 106 provided by the control member 2, as well as the ability to decouple the control member 2 from the access tube 102 to provide full access to the working channel 106 and to re-couple the control member 2 as needed, provides the surgeon with a multitude of options for advancing instrumentation to the treatment site.

Figure 6:
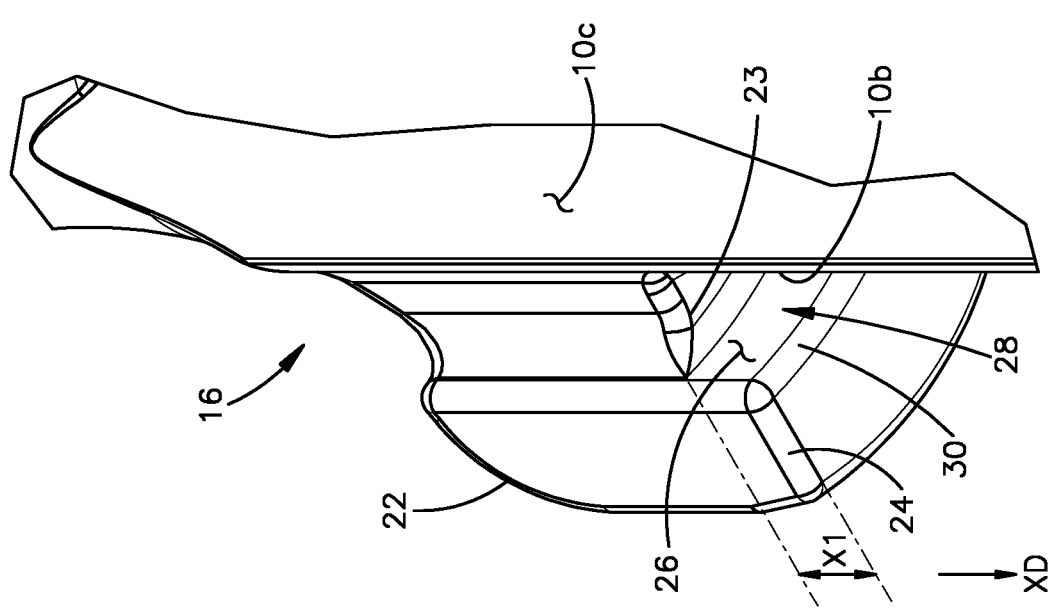
FIG. 6 is an enlarged perspective view of a portion of the mounting formation taken along region 6-6 in FIG. 5.

Referring now to FIG. 6, the lip 24 extends in the distal direction XD from the flange 22 to a distal lip surface 25. Accordingly, the lip 24 defines a lip overhang distance X1 measured between a distal surface 23 of the flange 22 to the distal lip surface 25 along the longitudinal direction X. The lip 24 defines an inner lip surface 26 that is opposed to the outer surface 10b of the post 20, such that mounting formation 16 defines a receptacle 28 that is located radially (i.e., located along the radial direction R) between the outer surface 10b and the inner lip surface 26 and extends in the proximal direction XP to the flange 22. The inner lip surface and the outer surface 10b can have complimentary arcuate profiles such that the receptacle 28 is at least partially annular. As shown, the receptacle 28 can extend annularly between the outer surface 10b and the inner lip surface 26 about the central axis 108. It should be appreciated that the receptacle 28 has a proximal depth defined by the lip overhang distance X1. It should also be appreciated that the receptacle 28 need not have an annular geometry. For example, in other embodiments, the inner lip surface 26 and/or the outer surface 10b of the post 20 can have a linear profile in a plane orthogonal to the central axis 108.

The distal surface 25 and the inner surface 26 can extend to a common (i.e., shared) boundary, such as a shared edge 30. As shown, the edge 30 can be radiused to facilitate insertion of the proximal end 110 of the access tube 102 during coupling. It should be appreciated that in some surgical procedures, the access tube 102 can be cut or otherwise trimmed to a desired length after it has been inserted to the target depth within the patient anatomy. Accordingly, one or more and up to each of the edge 30 and the inner and distal surfaces 26, 25 of the lip 24 can be configured as a guide surface to guide or "funnel" the cut proximal end 110 of the access tube 28 into a fully seated position within the receptacle 28. For example, in additional embodiments, one or more and up to each of the edge 30 and the inner and distal lip surfaces 26, 25 can be radiused, beveled, chamfered, or the like.

Referring now to FIG. 7, the receptacle 28 is sized to receive the proximal end 110 of the access tube 102, whereby the mounting formation 16 (and thus also the control member 2) interlocks with the proximal end 110 of the access tube 102. The major diameter D3 of the post 20 is preferably substantially equivalent to, or marginally less than, the inner diameter D4 a corresponding portion of the access tube 102, such that the outer surface 10b of the post 20 snugly fits to or engages with the inner surface 114 of the access tube 102 in the coupled configuration. Additionally, the post 20 and the lip 24 longitudinally overlap the access tube 102 at the proximal end 110 thereof, with the lip 24 overlapping the access tube 102 substantially by the lip overhang distance X1, and the post 20 overlapping the access tube 102 by a post overlap distance X2. The lip overhang distance X1 and the post overlap distance X2, combined with the snug fit of the post 20 within the access tube 102, provides a sturdy coupling between the control member 2 and the access tube 102. Moreover, the receptacle 28 defines a radial span R2, measured between the outer surface 10b and the inner lip surface 26. Preferably, the radial span R2 of the receptacle 28 is substantially equivalent to or marginally greater than the radial thickness R1 of a wall 102a of the access tube 102 at the proximal end 110 thereof, whereby the wall 102a at the proximal end 110 fits snugly within the recess 28 (i.e., between the outer surface 10b of the post 20 and the inner lip surface 26). The complimentary snug fits of the post 20 within the access tube 102 and the tube wall 102a within the recess 28 allows manipulation forces applied to the control member 2 to be transmitted to the access tube 102 substantially without "give" or "wobble" therebetween, which is important for precisely positioning (e.g., angulating and rotationally reorienting) the working channel 106.

Additionally, the post overlap distance X2 being shorter than the total length X0 of the access tube 102 provides space within a distal portion of the working channel (i.e., the space between the distal end 6 of the control member 2 and the distal end 112 of the access tube 102) for instrumentation, such as a camera for visualization of the treatment site, by way of a non-limiting example. Thus, the control member 2 of the present embodiment is configured to provide the camera with an unobscured view of the treatment site.

Figure 8:
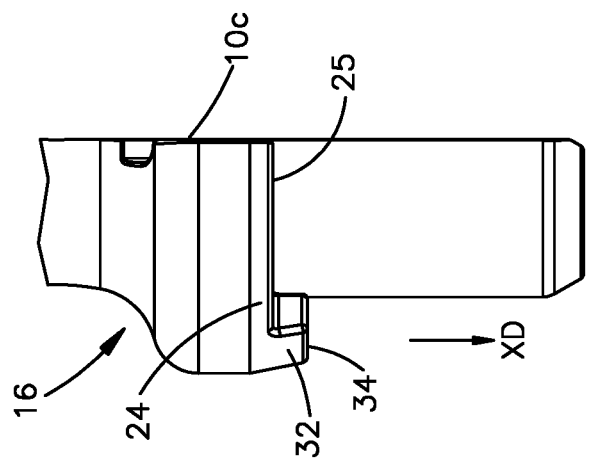
FIG. 8 is a side view of the mounting formation illustrated in FIG. 5.

Referring now to FIG. 8, the lip 24 can include an extension 32 on a side of the mounting formation 16 opposite the face 10c. Accordingly, the extension 32 defines a distal surface 34 spaced from the distal surface 25 of the lip 24 in the distal direction XD. The extension 32 is configured to provide additional support for the manipulation forces transmitted from the control member 2 to the access tube 102, and thereby and reduce the likelihood of wobble.

Figure 11:
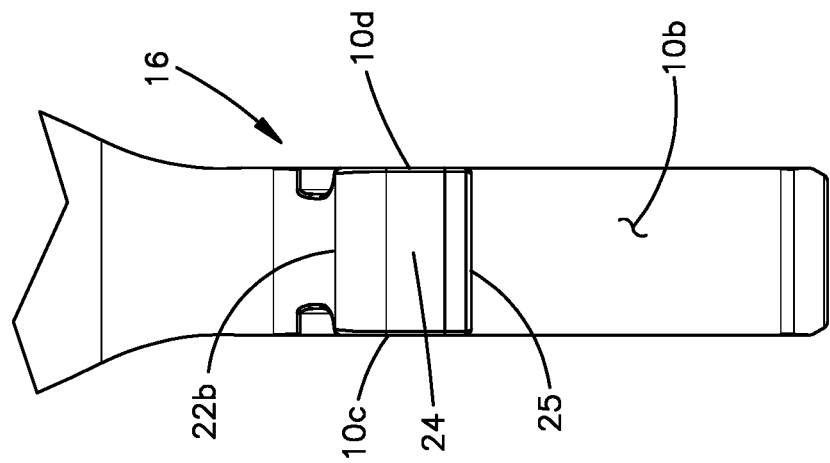
FIG. 11 is a side view of the mounting formation illustrated in FIG. 10.
Figure 10:
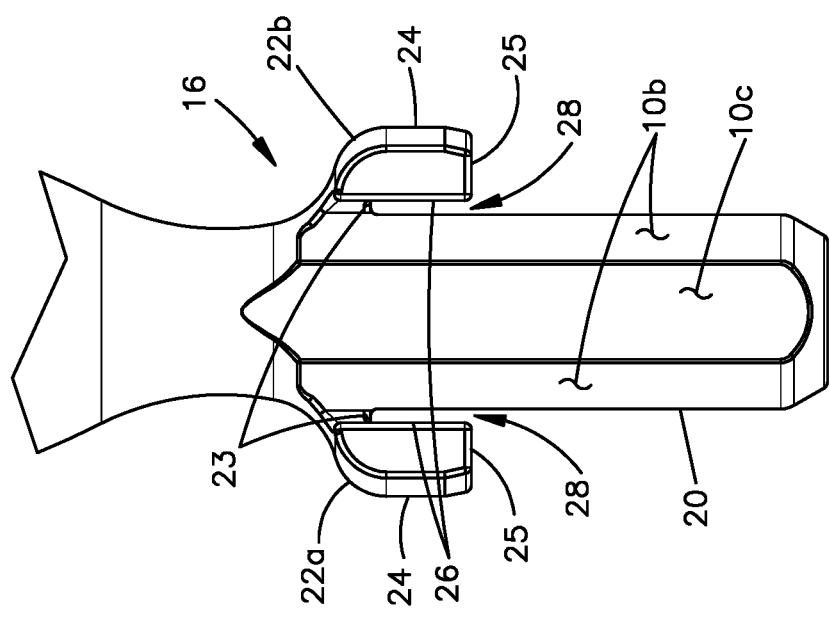
FIG. 10 is a front view of the mounting formation illustrated in FIG. 9.
Figure 9:
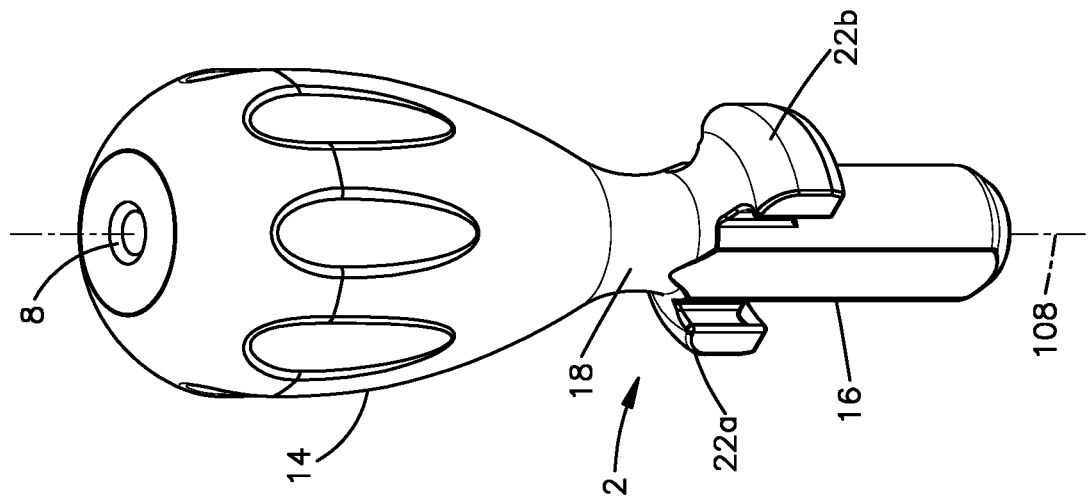
FIG. 9 is a perspective view of a control member having a mounting formation according to another embodiment of the present disclosure.

Referring now to FIGS. 9 and 10, in other embodiments, the mounting formation 16 can include a plurality of radial protrusions 22, such as a pair of opposed protrusions or wings 22a, b. It should be appreciated that the wings 22a, b of the present embodiment can each have a cross-sectional profile, in a sectional plane extending along the central axis 108, that is similar to the cross-sectional profile shown in FIG. 7. Accordingly, the wings 22a, b of the present embodiment each define a lip 24 that defines an inner lip surface 26 that is radially spaced (i.e., spaced along the radial direction) from the outer surface 10b of the post 20 by span R2. The lip 24 also extends in the distal direction XD from a distal surface 23 of the wing 22a, b to a distal lip surface 25. Thus, each wing 22a, b defines a receptacle 28 that is radially spaced between the inner lip surface 26 and the outer surface 10b of the post 20 and is configured to receive the proximal end 110 of the access tube 102, similarly as described above with reference to FIG. 7. Accordingly, the inner lip surfaces 26 and the outer surface 10b of the post 20 can define circumferential segments of an annulus about the post 20. Alternatively, the inner lip surface 26 and/or the outer surface 10b of the post 20 can have a linear profile in a plane orthogonal to the central axis 108. Additionally, as shown in FIG. 11, the mounting formation 16 of the present embodiment can define a first access surface or face 10c, and can also define a second face 10d opposite the first face 10c along the radial direction R. The opposed faces 10c, 10d can be configured substantially symmetrical to each other. It should be appreciated that the opposed faces 10c, 10d can each be configured similarly to that described above.

Figure 12:
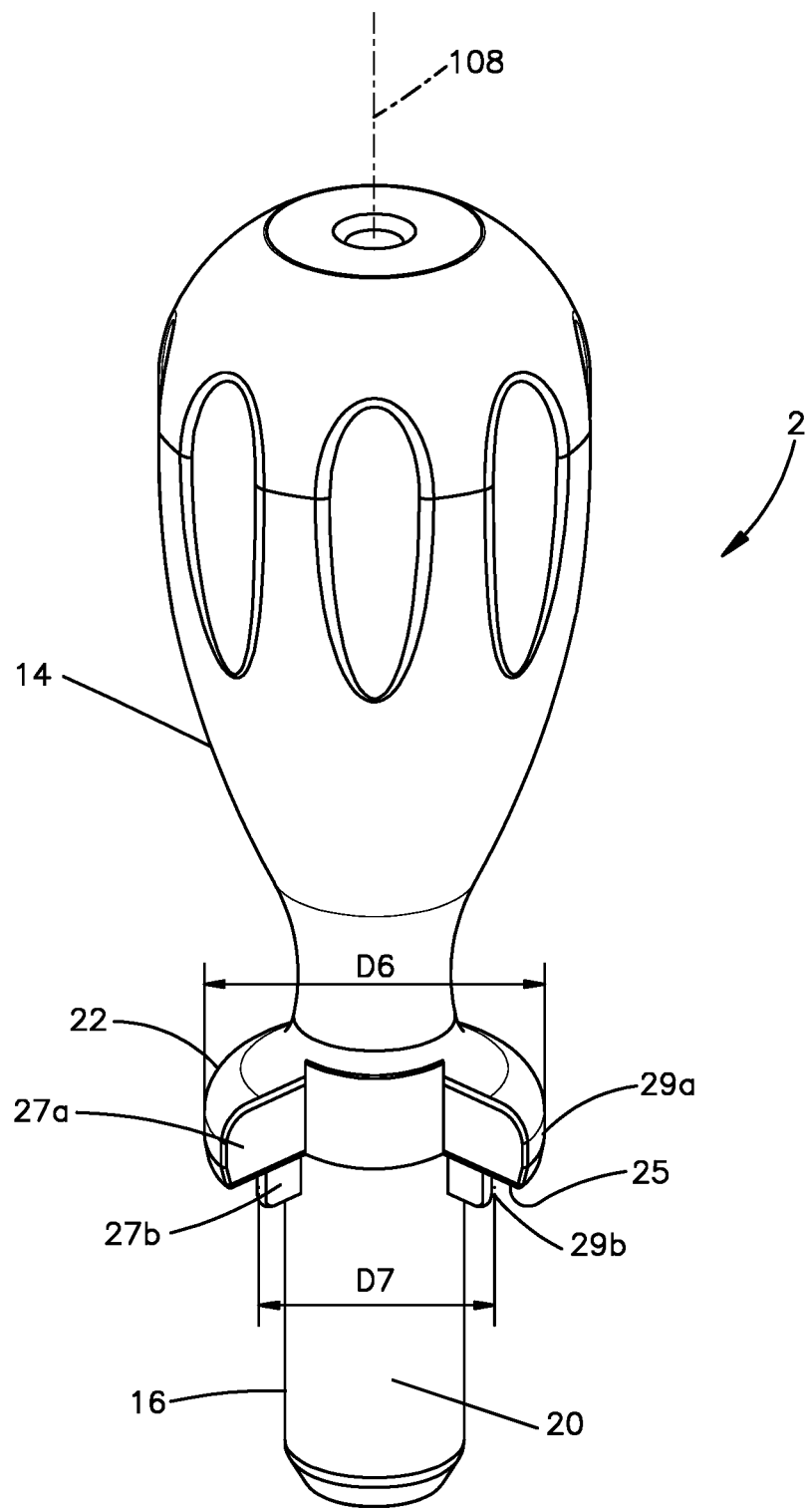
FIG. 12 is a perspective view of a control member having a mounting formation according to an additional embodiment of the present disclosure.

Referring now to FIG. 12, in additional embodiments, the mounting formation 16 can define a flange 22 having a step- or tier-like configuration. For example, as an alternative to the lips 24 described above, the flange 22 can define a proximal flange portion 27a and a distal flange portion 27b that extends from the proximal flange portion 27a in the distal direction XD. The proximal flange portion 27a can have an outer surface 29a that defines a first outer dimension D6, which, as shown, can be a first outer diameter D6. The proximal flange portion 27a defines a distal surface 25 that extends radially outward to the first outer surface 29a. The distal flange portion 27b has an outer surface 29b that defines a second outer dimension D7, such as a second outer diameter D7, that is less than the first outer dimension D6. The mounting formation 16 of the present embodiment is configured such that, when it is coupled to the access tube 102, the proximal end 110 of the access tube 102 abuts the distal surface 25 of the proximal flange portion 27a, and the second outer dimension D7 of the outer surface 29b of the distal flange portion 27b allows the distal flange portion 27b to fit snugly within with the inner surface 116 of the access tube 102, whereby the foregoing engagement allows manipulation forces to be transmitted from the control member 2 to the access tube 102.

It should be appreciated that the various features and geometries of the mounting formations 16 described throughout this disclosure, including but not limited to the flange 22, lips 24, lip surfaces 25, 26, edges 30, wings 22a, b, and flange portions 27a, b, can be tailored or otherwise adjusted as needed to interface with tubular bodies of various geometries.

It should also be appreciated that the bodies 3 of any of the control members 2 described above can optionally be a monolithic structure that defines each of the structural features of the control member 2. It should further be appreciated that the geometries of the structural features of the control members 2 described above allow for multiples uses and sterilization between each use.

The embodiments described above allow the post 20 to freely insert within and withdraw from the working channel 106 of the access tube 102 as needed. In this manner, the control member 2 can engage with the access tube 102 without the need for a separate locking mechanism to affix the control member 2 and the access tube 102 together. In other embodiments, however, the surgical access system 100 can include a separate locking mechanism for locking (at least temporarily) the control member 2 and the access tube 102 together. Such a separate locking mechanism can include, by way of a non-limiting example, an expandable collet connected to the post 20 and configured to expand into engagement with the inner surface 116 of the access tube 102 in a manner locking (e.g., temporarily) the control member 2 to the access tube 102. Other locking members are within the scope of the present disclosure.

Figure 13:
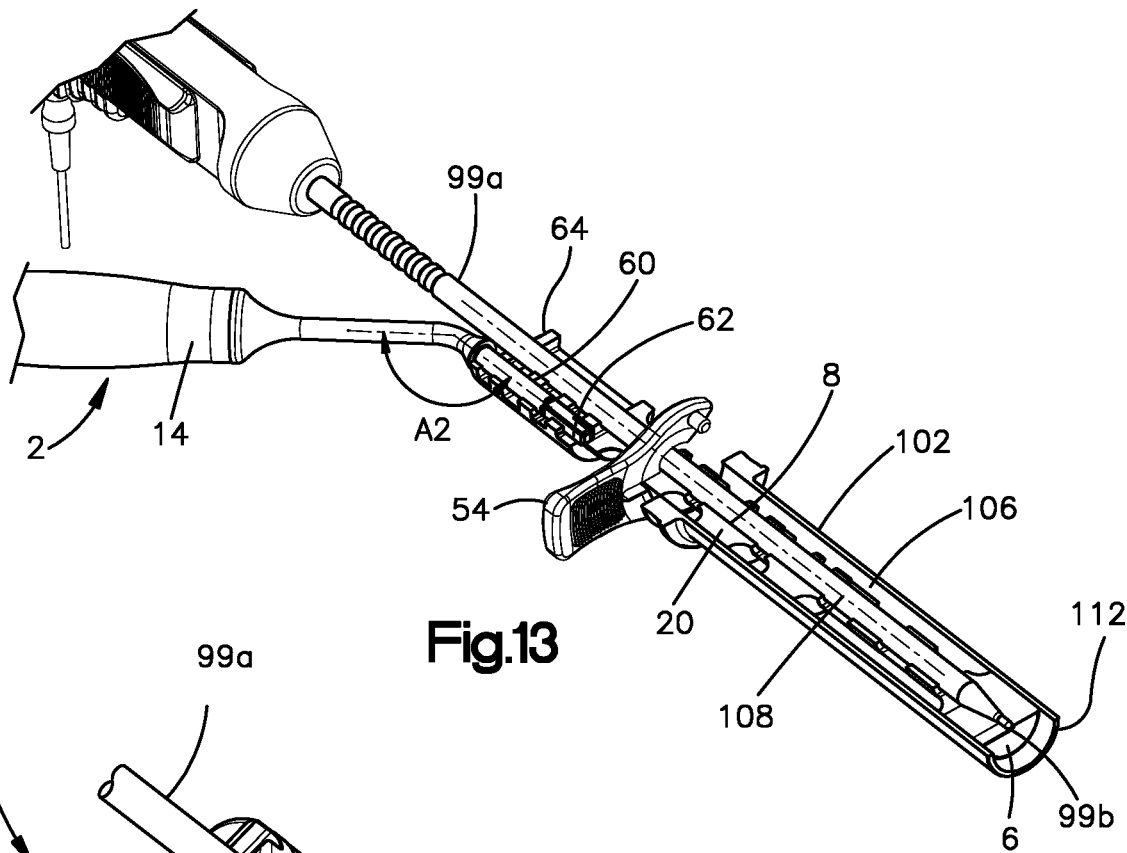
FIG. 13 is a partial sectional perspective view of a surgical access system for aligning a distal end of a navigated instrument with a distal end of the access tube, according to another embodiment of the present disclosure.
Figure 14:
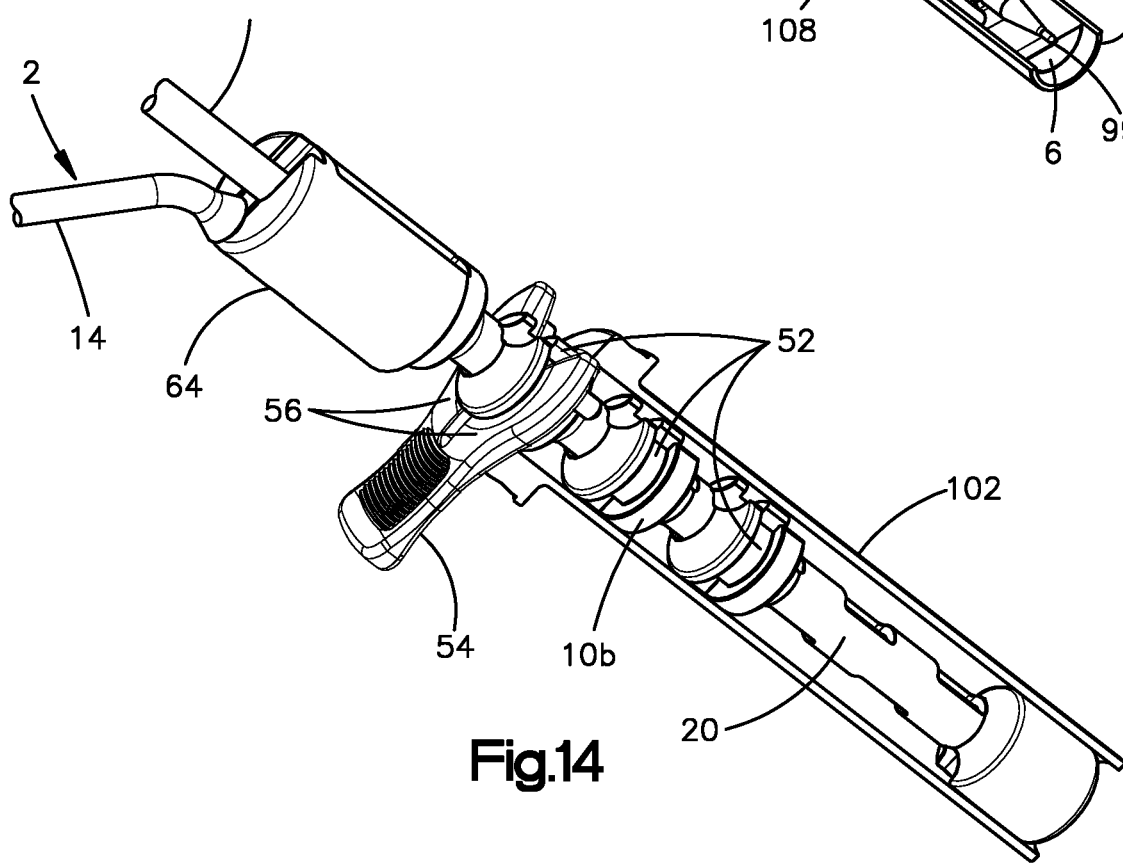
FIG. 14 is another partial sectional perspective view of the surgical access system illustrated in FIG. 13.

Referring now to FIGS. 13 and 14, in further embodiments, the control member 2 can have a handle portion 14 and an insertion portion 20 (or "post" or "plug" 20) that are oriented at an angle A2 relative to each other. In this manner, the handle portion 14 can be offset from the central axis 108 of the working channel 106 during use. The handle portion 14 and the plug 20 of the present embodiments can be monolithic with each other. Alternatively, as shown in FIG. 13, the handle portion 14 and the plug 20 can be separate components attached to one another. For example, the handle portion 14 can include a mounting post 60 configured for insertion within a channel 62 defined in a proximal, external portion 64 of the control member 2. In this manner, the plug 20 can be disposed within the working channel 106 of the access tube 102 and, after the access tube 102 has been located at the treatment site, the handle portion 14 can be detached from the plug 20 and optionally attached to a different plug 20 disposed in a different access tube 102 for manipulating that access tube 102 to an associated treatment site, for example. The mounting post 60 can be angularly offset from the remainder of the handle portion 14 by angle A2.

The plug 20 can be configured so that its distal end 6 is coincident with the distal end 112 of the access tube 102. The plug 20 can define a central axis 108 and a central bore 8 that extends along the central axis 108. The central bore 8 is configured to receive an instrument, such as the multi-tool 99a described above and in the '253 Reference, which can be used for navigation. The central bore 8 and the multi-tool 99a can have complimentary geometries configured to maintain the multi-tool 99a parallel with the central axis 108. The complimentary geometries between the central bore 8 and the multi-tool 99a can also be configured to effectively affix or lock a distal end 99b of the multi-tool 99a at a longitudinal location coincident with the distal end 112 of the access tube 102. In this manner, the distal end of the multi-tool 99a can indicate or otherwise provide visualization of the position of the distal end 112 of the access tube 102 under x-ray imagery and/or fluoroscopy, such as for navigating the access tube 102 to the target location at or adjacent the intended surgical treatment site. Optionally, the distal end 6 of the control member 2 can also be coincident with the distal ends 112, 99b of the access tube 102 and the multi-tool, respectively.

The control member 2 of the presently illustrated embodiments can be configured for selective insertion within a plurality of access tubes 102 having discrete lengths along the longitudinal direction X. Such a plurality of access tubes 102 can be provided in a kit, such as a surgical access kit, which can also include one or more instruments, such as one or more multi-tools 99a and/or other instruments for navigation and imaging, by way of non-limiting examples. In embodiments where the handle portion 14 and the plug 20 are separate components connectable to each other, the kit can include at least one plug 20 and one or more handle portions 14, such as a plurality of handle portions 14 having different geometries and each configured to connection to the at least one plug 20.

The plug 20 can be configured for selective insertion within any of the plurality of access tubes 102 having discrete lengths. For example, the plug 20 can include a series of mounting structures, such as mounting grooves 52, longitudinally spaced from each other by common intervals that correspond to the discrete lengths of the access tubes 102. The mounting grooves 52 can have an annular or semi-annular configuration along the outer surface 10b of the plug 20 and can be configured to receive a complimentary mounting structure of a locking member, such as flexible arms 56 of a locking clip 54. The control member 2 can be configured so that, for any of the plurality of access tubes 102 of discrete lengths, the locking clip 54 can be inserted into the mounting groove 52 adjacent the proximal end 110 of the access tube 102. It should be appreciated that other types of locking members can be employed with the control member 2 of the present embodiment. In other embodiments, the kit can include a plurality of plugs 20 having discrete lengths and each configured for use with a respective one of the access tubes 102 of discrete length.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A control member body for mounting to an end of an access tube, comprising:
   a proximal end and a distal end spaced from each other along a central axis,
   a bore extending from the proximal end to the distal end along the central axis, the bore configured to receive instrumentation;
   a handle portion extending to the proximal end;
   an insertion portion that extends to the distal end and is configured to be inserted within the access tube, the insertion portion comprising:

an outer surface that defines a part of a cylinder, the outer surface defining a major diameter insertion portion; and an exterior access surface that is substantially planar and is spaced from the bore along a radial direction perpendicular to the central axis, the exterior access surface defining a minor distance along the radial direction, wherein the minor distance is less than the major diameter such that the exterior access surface is configured to at least partially define an opening into the access tube when the insertion portion resides within the access tube and the outer surface of the insertion portion engages an inner surface of the access tube; and a lip opposed to the outer surface of the insertion portion so as to define a receptacle therebetween along the radial direction, wherein the receptacle is configured to receive an end portion of the access tube.

2. The control member body of claim 1, wherein the bore is centrally located within the control member body, and the central axis extends centrally through the bore.

3. The control member body of claim 1, wherein the control member body includes a protrusion extending outwardly from the insertion portion along the radial direction, and the lip extends distally from the protrusion.

4. The control member body of claim 1, wherein the lip defines an inner lip surface that faces the outer surface of the insertion portion, and the inner lip surface and the outer surface have complementary arcuate shapes such that the receptacle is semi-annular.

5. A method of adjusting a position of an access tube that extends distally through a skin line and to a target location within a patient anatomy, the method comprising:

attaching a control member to a proximal end of the access tube such that a central axis of the control member extends through a working channel of the access tube, wherein the central axis is spaced from each inner surface of the access tube at the conclusion of the attaching step, the control member defining a bore extending through the control member along the central axis, wherein the attaching step comprises inserting an insertion portion of the control member within the working channel, such that:

the proximal end of the access tube is received within a receptacle of the control member, the receptacle defined between a lip of the control member and the insertion portion along a radial direction perpendicular to the central axis, an outer surface of the insertion portion engages a circumferential portion of the inner surface of the access tube, and an exterior access surface of the insertion portion is radially spaced from a portion of the inner surface that is radially opposed to the circumferential portion of the inner surface of the access tube so as to define an opening into the working channel, wherein the outer surface defines part of a cylinder, and the exterior access surface is substantially planar and is radially spaced from the bore; and manipulating the control member, thereby responsively adjusting a trajectory of the working channel relative to the patient anatomy.

6. The method of claim 5, wherein the manipulating step further comprises rotating the control member about the central axis, thereby responsively rotating the access tube about the central axis.

7. The method of claim 5, wherein the manipulating step comprises angulating the control member about a pivot axis substantially perpendicular to the central axis, thereby responsively angulating the access tube about the pivot axis.

8. The method of claim 7, the manipulating step further comprises angulating the control member polyaxially about the pivot axis and at least one additional pivot axis that is substantially perpendicular to the central axis and offset from the pivot axis, thereby responsively angulating the access tube polyaxially.

9. The method of claim 8, wherein the manipulating step further comprises rotating the control member about the central concurrently with the angulating of the control member polyaxially, thereby responsively concurrently rotating the access tube about the central axis and angulating the access tube polyaxially.

10. The method of claim 5, wherein the manipulating step causes a distal end of the access tube to contact a facet line of adjacent vertebral bodies.

11. The method of claim 10, wherein at the conclusion of the manipulating step the central axis extends through an intervertebral disc space between the adjacent vertebral bodies.

12. The method of claim 5, further comprises trimming a proximal region of the access tube before the attaching step, wherein the proximal end of the access tube during the attaching step is a trimmed proximal end of the access tube.

13. The method of claim 5, further comprising, after the manipulating step, advancing a navigated instrument distally through the bore and the working channel and into a treatment site associated with the target location.

14. The method of claim 13, wherein the navigated instrument has an outer diameter that is complementary with an interior surface of the control member within the bore, such that the step of advancing the navigated instrument distally through the bore substantially aligns a longitudinal axis of the navigated instrument with the central axis.

15. The method of claim 13, further comprising advancing a camera through the opening and into the working channel.

16. The method of claim 13, further comprising advancing one or more irrigation tubes through the opening and into the working channel.

17. The method of claim 13, wherein the control member is formed of radiolucent material, and the method further comprises viewing the navigated instrument and the treatment site under radioscopy.

18. The method of claim 5, further comprising:
detaching the control member from the access tube; and
advancing one or more surgical instruments distally through the access tube.

19. The method of claim 18, further comprising re-attaching the control member to the proximal end of the access tube.

20. The method of claim 19, further comprising, after the re-attaching step, further manipulating the control member, thereby responsively further adjusting the trajectory of the working channel relative to the patient anatomy.

* * * * *